US009932352B2

(12) United States Patent
Guarna et al.

(10) Patent No.: US 9,932,352 B2
(45) Date of Patent: Apr. 3, 2018

(54) COMPOUNDS FOR THE TREATMENT OF ISCHEMIA-REPERFUSION-RELATED DISEASES

(71) Applicant: MINERVA PATENTS S.A., Luxembourg (LU)

(72) Inventors: Antonio Guarna, Seravezza (IT); Federico Cozzolino, Fiesole (IT)

(73) Assignee: MINERVA PATENTS S.A., Luxembourg (LU)

( * ) Notice: Subject to any disclaimer, the term of this patent is extended or adjusted under 35 U.S.C. 154(b) by 0 days.

(21) Appl. No.: 14/387,015

(22) PCT Filed: Mar. 20, 2013

(86) PCT No.: PCT/IB2013/052205
§ 371 (c)(1),
(2) Date: Sep. 22, 2014

(87) PCT Pub. No.: WO2013/140348
PCT Pub. Date: Sep. 26, 2013

(65) Prior Publication Data
US 2015/0080388 A1    Mar. 19, 2015

(30) Foreign Application Priority Data
Mar. 21, 2012  (IT) .............. FI2012A0062

(51) Int. Cl.
*C07D 498/08* (2006.01)
*G01N 33/50* (2006.01)
(52) U.S. Cl.
CPC ....... *C07D 498/08* (2013.01); *G01N 33/5005* (2013.01)
(58) Field of Classification Search
CPC .................................. C07D 498/08
See application file for complete search history.

(56) References Cited

U.S. PATENT DOCUMENTS 4,463,004 A    7/1984  Guerret et al.
7,625,892 B2   12/2009 Guarna et al.
2003/0176414 A1 9/2003  Guarna et al.

FOREIGN PATENT DOCUMENTS

EP    1130022 A1   9/2001
WO    0164686 A1   9/2001
WO    2004000324 A1 12/2003
WO    2004009588 A1 1/2004

OTHER PUBLICATIONS

Registry No. 1219697-02-5, File Registry, entered STN Apr. 20, 2010.*
Registry No. 1219697-03-6, File Registry, entered STN Apr. 20, 2010.*
Reymond et al., "New Chiral auxiliaries and new optically pure ketene equivalents derived from tartaric acids. Improved synthesis of (−)-7-oxabicyclo[2.2.1]hept-5-en-2-one"; Tetrahedron Asymmetry, Pergamon Press Ltd, Oxford, GB, vol. 1, No. 10, Jan. 1, 1990.
Mannino C. et al.; "Synthesis of bicyclic molecular scaffolds (BTAa): An investigation towards new selective MMP-12 inhibitors", Bioorganic & Medicinal Chemistry, Pregamon, GB, Nov. 15, 2006.
Guarna A. et al., "Synthesis and Reactivity of Bicycles Derived from Tartaric Acid and alpha-Amino Acids: A Novel Class of Conformationally Constrained Dipeptide Isosteres Based upon Enantiopure 3-Aza-6, 8-dioxabicyclo [3.2.1] octane-7-carb oxylic Acid", Journal of Organic Chemistr, American Chemical Society, Easton, U.S.; vol. 64, No. 20, Jan. 1, 1999.
Andrea Trabocchi et al: "Diastereoselective Synthesis of Highly Constrained Spiro-[beta]—Lacatms by the Staudinger Reaction Using an Unsymmetrical Bicyclic Ketene"; European Journal of Organic Chemistry, vol. 2007, No. 27, Sep. 1, 2007.
International Search Report for PCT/IB2013/052205 dated Aug. 7, 2013.
Guarna, et al., J. Org. Chem., 64:7347-7364 (1999).
Machetti, et al., Organic Letters, 2:25:3987-3990 (2000).
Scarpi, et al., Bioorganic & Medicinal Chemistry, 9:1625-1632 (2001).
Cini, et al., Eur. J. Org. Chem., 2002:873-880 (2002).
Trabocchi, et al., Eur. J. Org. Chem., 2007:27:4594-4599 (2007).
Wang, et al., J. Chem. Soc., Perkin Trans. I, 209-212 (1996).
Guarna, et al., Tetrahedron: Asymmetry, 11:4227-4238 (2000).
Guidi, et al., Arch. Pharm. Pharm. Med. Chem., 330-201-202 (1997).
May, et al., Journal of Pharmaceutical Sciences, 57(3):511-513 (1968).
Van Cauwenberghe, et al., Heterocycles, 3(2):101-107 (1975).

* cited by examiner

*Primary Examiner* — Rebecca L Anderson
(74) *Attorney, Agent, or Firm* — Abelman, Frayne & Schwab

(57) ABSTRACT

The present invention relates to compounds of formula (I) useful in the treatment of ischemia-reperfusion-related pathologies.

15 Claims, 4 Drawing Sheets

COMPOUNDS FOR THE TREATMENT OF ISCHEMIA-REPERFUSION-RELATED DISEASES

CROSS REFERENCE TO RELATED APPLICATION

This application is a national phase of Application No. PCT/IB2013/052205 filed Mar. 20, 2013, and claims priority from Italian Patent Application No. FI2012A000062 filed Mar. 21, 2012.

FIELD OF THE INVENTION

The present invention relates to the field of compounds useful in the treatment of ischemia-reperfusion-related pathologies.

BACKGROUND OF THE INVENTION

Ischemia-reperfusion is a pathological condition characterised by an initial restriction of blood flow to an organ followed by a subsequent restoration of perfusion and concomitant re-oxygenation. Perhaps surprisingly, restoration of the blood flow and re-oxygenation is frequently associated with an increase in tissue damage and a profound inflammatory response ("reperfusion injury"). Ischemia-reperfusion injury exists in a wide range of pathological conditions (Table 1).

TABLE 1

| Affected organ | Example of clinical manifestation |
| --- | --- |
| Ischemia-reperfusion of individual organs | |
| Heart | Acute coronary syndrome |
| Kidney | Acute hypoxic renal injury |
| Intestine | Intestinal ischemia-reperfusion; MODS |
| Brain | Stroke |
| Ischemia/reperfusion of multiple organs | |
| Trauma and resuscitation | MODS; acute hypoxic renal injury; hypoxic intestinal injury; CTE |
| Circulatory arrest | Hypoxic cerebral injury; MODS; kidney damage |
| Sickle cell anaemia | Acute thoracic syndrome; pulmonary hypertension; acute hypoxic renal injury |
| Sleep apnoea | Hypertension; diabetes |
| Ischemia-reperfusion in the course of surgery | |
| Cardiac surgery | Acute heart failure following cardiopulmonary bypass |
| Thoracic surgery | Acute hypoxic pulmonary injury |
| Peripheral vascular surgery | CSE |
| Vascular surgery | Acute hypoxic renal injury Acute transplant rejection; early transplant rejection |

MODS (Multiple Organ Dysfunction Syndrome): Multiple organ dysfunction syndrome;
CSE (Compartment Syndrome of the Extremity): Compartment syndrome of the extremities
CTE (chronic traumatic encephalopathy): chronic traumatic encephalopathy caused by trauma from repeated blows (e.g., boxers, rugby players etc.)

The above-described ischemia-reperfusion-related pathological conditions derive from a set of biochemical events at cellular and tissue level. Once the blood flow has stopped in a given district, at a branch of the coronary artery for example, a series of biochemical processes takes place within the cells of the non-perfused tissues. While in the face of complete anoxia some of them undergo necrosis, the majority undergo a profound metabolic imbalance that is essentially characterised by a rapid increase of the intracellular content of reactive oxygen species (ROS, which include superoxide anion, $O_2^-$, hydrogen peroxide and the hydroxyl radical), by the low levels produced by the electron transport chain at amounts harmful to the cell. If the blood flow is restored (i.e. reperfusion), as occurs after angioplasty surgery, the amount of free radicals further increases, giving rise to extensive cell damage, which configures the "ischemia-reperfusion" condition. This situation, which is essentially a massive redox shock, is not only directly harmful to various macromolecules within the cell (proteins, nucleic acids, lipids), but is capable of triggering the intrinsic pathway of apoptosis.

Indeed, in myocardial infarction, up to 80% of the extension of the final lesion is linked to apoptotic death, which completes in hours to days following the onset of the ischemia-reperfusion condition.

From a biochemical viewpoint, the intense metabolic shock activates a large number of molecules that act as redox sensors, such as ASK-1 kinase. This kinase is maintained in an inactive state by the bond with reduced thioredoxin and glutaredoxin; the oxidation thereof determines their detachment from ASK-1 and the consequent functional activation of the kinase.

Other pathways involved from the outset of the process include AMP kinase and Rho GTPase. Operating in synergy, these systems can reciprocally influence each other, thus significantly amplifying the apoptotic process. A functionally coherent family of kinases located downstream of the above-described metabolic pathways, consists of the JNK and p38 MAPK (MAP-kinase) proteins, which represent a common node of the chain of signal transmission chain. These molecules have cytosolic and nuclear substrates, that are in part shared, which participate in various ways to the processes of cell death by autophagy or apoptosis. To cite a few examples, JNK and p38 MAPK bind and phosphorylate Bcl-xL and Bcl-2, inactivating the anti-apoptotic potential thereof, an event followed by the release of cytochrome c from the mitochondrion, the combination thereof with molecule Apaf-1 and the consequent activation of caspase-9. Other critical targets of the two MAP-kinases are Beclin-1 and p53, both closely related to the onset of autophagic and apoptotic cell death, respectively.

On the basis of the above-reported considerations, it can be stated that the MAP-kinase are critical for the generation of the cell damage that takes place in a number of clinical contexts, in particular in conditions of ischemia-reperfusion. It is also interesting to note that p38 MAPK and JNK share a common biochemical modulator, MKP-1, a phosphatase specifically capable of inactivating the MAP-kinase enzyme family.

A number of studies have directly demonstrated this statement; for example, knock-out mice for p38 MAPK, following the closure of branches of the coronary artery, have greatly reduced myocardial lesions with respect to the normal controls, a finding that emphasises the role of these kinases in the generation of tissue damage.

It is thus in the state of the art that for the treatment of ischemia-reperfusion-related pathologies or for the use in medical procedures involving ischemia-reperfusion, a useful pharmacological approach can be achieved through the use of compounds that are capable of modifying the activity of the MAP kinases family. Patent WO2004000324 sets out that 3-azabicyclo[3.2.1]octan derivatives are active as agonists of human neurotrophins and are therefore useful for the preparation of pharmaceutical compositions for the treatment of diseases in which the neurotrophin functions, particularly NGF functions, are implicated by default:

neurodegenerative disorders of the central nervous system, such as Alzheimer's disease (AD), amyotrophic lateral sclerosis (ALS), Huntington's disease, neuropathies, neural damage caused by hypoxia, ischemia, or trauma, inducing apoptosis of the nerve cells;

acquired immunodeficiency diseases linked to reduced bioavailability of NGF, such as age-related immunodeficiency; diseases in which neoangiogenesis stimulation proves advantageous, such as myocardial infarction, stroke, or peripheral vascular diseases;

certain diseases of the eye, such as keratitis of diverse aetiology, glaucoma, degenerative or inflammatory conditions of the retina.

has been described as intermediate for the synthesis of a spiro-beta-lactam in A. Trabocchi, et al. Eur. J. Org. Chem. 2007, 4594-4599.

The (1R,5S,7R)-3-(p-methoxybenzyl)-2-oxo-6,8-dioxa-3-azabicyclo[3.2.1]octan-7-carboxylic Acid compound has been described as peptidomimetic in Antonio Guarna, et al J. Org. Chem. 1999, 64, 7347-7364.

The (1R,5S,7R)-3-Benzyl-2-oxo-6,8-dioxa-3-azabicyclo[3.2.1]octan-7-carboxylic Acid compound and the (1R,5S,7R)-3-(p-phenyl)-benzyl-2-oxo-6,8-dioxa-3-azabicyclo[3.2.1]octan-7-carboxylic Acid compound were described as inhibitors of metalloproteases in C. Mannino et al. Bioorganic & Medicinal Chemistry 14 (2006) 7392-7403.

The synthesis of the (1S,5R,7S)-3-ethyl-2-oxo-6,8-dioxa-3-azabicyclo[3.2.1]octan-7-carboxylic acid compound is described in Reymond, J-L.; et al. Tetrahedron Asymmetry 1990, 1(10), 729-736.

The object of the present invention is to provide compounds for the treatment of ischemia-reperfusion-related pathologies or for use in medical procedures involving ischemia-reperfusion, and in particular, but not exclusively, those characterised by an inappropriate variation in the activities of the MAP kinases family.

SUMMARY OF THE INVENTION

Object of the present invention are compounds of formula (I)

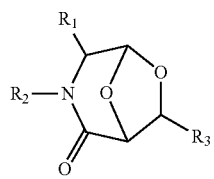

I wherein
$R_1$ is selected from the group consisting of H, $C_{1-8}$alkyl, $C_{1-8}$alkenyl, $C_{2-8}$alkynyl, cycloalkyl, aryl, heterocycle —$C_{1-8}$alkyl-aryl, —$C_{1-8}$alkyl-heterocycle, —$C_{1-8}$alkyl-NH2, -aryl-NH2, —$C_{1-8}$ alkyl-O-aryl-aryl-OH, $C_{1-8}$alkyl-OH, —COOR, —$C_{1-8}$alkyl-OR, methyloxycarbonyl-$C_{1-8}$alkyl, carboalkyloxy-aryl, alkyl carbamoyl aryl and -(amino acid side chains);

$R_2$ is selected from the group consisting of H, $C_{1-8}$alkyl, $C_{2-8}$alkenyl, $C_{2-8}$alkynyl, cycloalkyl, aryl, —$C_{1-8}$alkyl-aryl, —$C_{1-8}$alkyl-heterocycle, —$C_{1-8}$alkyl-NRR', -aryl-NRR', —$C_{1-8}$alkyl-OR, —$C_{1-8}$alkyl-COOR, —$C_{1-8}$alkyl-OC(O)R, —$C_{1-8}$alkyl-N(R)C(O)R', -aryl-OR, -aryl-COOR, -aryl-COR, -aryl-OC(O)R, -aryl-N(R)C(O)R', —CH(amino acid side chains)$CO_2R$, —CH(amino acid side chains)C(O)NR), —CH($CO_2R$)-amino acid side-chains and CH(CONRR')-amino acid side chains, $R_3$ is COOH;

R and R', equal or different from each other, are selected from the group consisting of H, $C_{1-8}$alkyl, $C_{2-8}$alkenyl, $C_{2-8}$alkynyl, cycloalkyl, aryl, heterocycle, —$C_{1-8}$alkyl-aryl; —$C_{1-8}$alkyl-heterocycle; protecting group, —C(O)CH-(amino acid side-chains)-NHT, —NH—CH(amino acid side chains)COOT and —CH(amino acid side chains)COOT, where T is selected from H and $C_{1-8}$alkyl;

and where the above-reported alkyl, alkenyl, alkynyl, cycloalkyl, aryl, heterocycle groups can be substituted with one or more groupings selected from the group consisting of halogen, CN, NO2, NH2, OH, COOH, CO and $C_{1-6}$alkyl;

excluding the (1S,5R,7S)-3-ethyl-2-oxo-6,8-dioxa-3-azabicyclo[3.2.1]octan-7-carboxylic acid, (1R,5S,7R)-3-(p-methoxybenzyl)-2-oxo-6,8-dioxa-3-azabicyclo[3.2.1]octan-7-carboxylic acid, (1R,5S,7R)-3-benzyl-2-oxo-6,8-dioxa-3-azabicyclo[3.2.1]octan-7-carboxylic acid and (1R,5S,7R)-3-(p-phenyl)-benzyl-2-oxo-6,8-dioxa-3-azabicyclo[3.2.1]octan-7-carboxylic acid compounds.

In the course of studies aimed at clarifying the pathogenetic mechanisms generated from the uncontrolled activation of the MAP-kinase enzyme, in clinical conditions determined by ischemia-reperfusion, it was surprisingly and unexpectedly found that an effective control of the activation of p38 MAKP or of JNK could be obtained from the in vitro and in vivo administration of certain derivatives of 3-azabicyclo[3.2.1]octan of general formula (I) as described above and other similar compounds belonging to the collections of compounds that were the subject of patent WO2004000324.

Compounds of formula (I) as described above (with R3=COOH), also including the (1S,5R,7S)-3-ethyl-2-oxo-6,8-dioxa-3-azabicyclo[3.2.1]octan-7-carboxylic acid, (1R,5S,7R)-3-(p-methoxybenzyl)-2-oxo-6,8-dioxa-3-azabicyclo[3.2.1]octan-7-carboxylic acid, (1R,5S,7R)-3-Benzyl-2-oxo-6,8-dioxa-3-azabicyclo[3.2.1]octan-7-carboxylic acid and (1R,5S,7R)-3-(p-phenyl)-benzyl-2-oxo-6,8-dioxa-3-azabicyclo[3.2.1]octan-7-carboxylic acid compounds, for use as a medicament, are thus also object of the invention.

A derivative compound of 3-azabicyclo[3.2.1]octan of general formula (I) is also therefore object of the present invention:

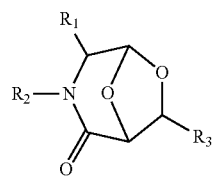

I wherein
$R_1$ is selected from the group consisting of H, $C_{1-8}$alkyl, $C_{1-8}$alkenyl, $C_{2-8}$alkynyl, cycloalkyl, aryl, heterocycle —$C_{1-8}$alkyl-aryl, —$C_{1-8}$alkyl-heterocycle, —$C_{1-8}$alkyl-NH2, -aryl-NH2, —$C_{1-8}$alkyl-O-aryl, -aryl-OH, $C_{1-8}$alkyl-OH, —COOR, —$C_{1-8}$alkyl-OR, methyloxycarbonyl-$C_{1-8}$alkyl, carboalkyloxy-aryl, alkyl carbamoyl aryl and -(amino acid side chains);

$R_2$ is selected from the group consisting of H, $C_{1-8}$alkyl, $C_{2-8}$alkenyl, $C_{2-8}$alkynyl, cycloalkyl, aryl, —$C_{1-8}$alkyl-aryl, —$C_{1-8}$alkyl-heterocycle, —$C_{1-8}$alkyl-NRR', -aryl-NRR', —$C_{1-8}$alkyl-OR, $C_{1-8}$alkyl-COOR, $C_{1-8}$alkyl-OC(O)R, —C$_{1-8}$alkyl-N(R)C(O)R', -aryl-OR, -aryl-COOR, -aryl-COR, -aryl-OC(O)R, -aryl-N(R)C(O)R', —CH(amino acid side chains)CO$_2$R, —CH(amino acid side chains)C(O)NR), —CH(CO$_2$R)-amino acid side-chains and CH(CONRR')-amino acid side chains, R$_3$ is selected from the group consisting of H, C$_{1-8}$alkyl, C$_{2-8}$alkenyl, C$_{2-8}$alkynyl, cycloalkyl, aryl, —C$_{1-8}$alkyl-aryl, heterocycle, —C$_{1-8}$alkyl-heterocycle; —C(O)R, —C(O)OR, —C(O)NRR', CH$_2$OR, CH$_2$NRR', —C(O)NH—CH(amino acid side chains)C(O)OR, CH$_2$NRFmoc, CH$_2$NR-Boc and CH$_2$NR—CBz, R and R', equal or different from each other, are selected from the group consisting of H, C$_{1-8}$alkyl, C$_{2-8}$alkenyl, C$_{2-8}$alkynyl, cycloalkyl, aryl, heterocycle, —C$_{1-8}$alkyl-aryl; —C$_{1-8}$alkyl-heterocycle; protecting group, —C(O)CH-(amino acid side-chains)-NHT, —NH—CH(amino acid side chains)COOT and —CH(amino acid side chains)COOT, where T is selected from H and C$_{1-8}$alkyl;

and where the above-reported alkyl, alkenyl, alkynyl, cycloalkyl, aryl, heterocycle groups can be substituted with one or more groupings selected from the group consisting of halogen, CN, NO2, NH2, OH, COOH, CO and C$_{1-8}$alkyl;

for the treatment of ischemia-reperfusion-related pathologies or for use in medical procedures involving ischemia-reperfusion, and in particular, but not exclusively, those characterised by an inappropriate variation in the activity of the MAP kinase family.

In particular, the 3-azabicyclo[3.2.1]octan derivatives of general formula (I), unexpected and unpredictably determine a marked increase in the MKP-1 protein in a certain number of cell types that express Trk receptors (in particular, cardiomyocytes, neural cells, renal parenchymal cells, etc.); this event was achieved in the absence of a significant activation of other metabolic pathways, such as, for example, the phosphatidylinositol-3 kinase/protein-kinase B pathway, which leads to increased intracitosolic calcium levels. Human memory B lymphocytes deprived of their autocrine survival factor, NGF, undergo a strong activation of p38 MAPK, followed by the apoptotic death of the cells. This damage is profoundly reduced by the addition of 3-azabicyclo[3.2.1]octan derivatives of general formula (I), which cause a marked increase in MKP-1 levels and an intense modulation of p38 MAPK; consequently, the cells are protected from programmed death. In the same way, myocardial cells cultured for 30 minutes under profoundly hypoxic conditions (pO$_2$<0.1%), then brought to normal oxygen levels, undergo a marked redox shock, characterised by activation of p38-MAPK, activation of caspase and apoptosis. Nevertheless, if 3-azabicyclo[3.2.1]octan derivatives of general formula (I), are administered before the hypoxia or immediately thereafter, the intensity of the redox alterations remains unchanged, but p38 MAPK phosphorylation is profoundly reduced and apoptosis controlled; indeed, in the same cultures there is recorded a parallel, marked increase of MKP-1 protein levels. The above-descried studies demonstrate a possible biological approach addressed at mitigating the outcomes of the uncontrolled activation of MAP-kinase family proteins, which is potentially useful in a number of clinical conditions characterised by ischemia-reperfusion, in which there in particular occurs, an inappropriate variation in the activity of the MAP kinase family.

These unexpected findings allow identification of the pharmacological use of the 3-azabicyclo[3.2.1]octan derivatives of general formula (I) in all those ischemia-reperfusion-related pathologies, in which the ischemic conditions generated from any reduction or cessation of the blood flow, are followed by subsequent restoration of the influx of oxygen/nutrients to the tissue.

Further characteristics and advantages of the compounds according to the invention will be reported in detail in the following description.

DETAILED DESCRIPTION OF THE INVENTION

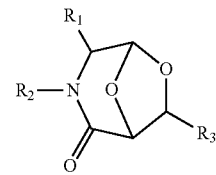

A further object of the present invention is therefore a pharmaceutical composition comprising as active ingredient at least one of the 3-azabicyclo[3.2.1]octan derivatives of general formula (I) as described above for the treatment of ischemia-reperfusion-related pathologies In particular, ischemia-reperfusion-related pathologies as defined above are for example:

acute myocardial ischemia;

central nervous system (CNS) ischemia caused by thrombosis or embolism of the intracranial arteries or by cardiac arrest, involving the permanent or temporary interruption of the blood flow in some cerebral arterial districts or in the whole encephalon;

surgical procedures wherein the operation provides for certain arterial districts to be temporarily closed, as for example occurs in renal tumour ablation surgery;

explant, preservation and reimplantation protocols for organs intended for transplantation, such as kidneys, heart, lung, liver, intestine, etc.;

all the other ischemic pathologies characterised by a reduction or cessation of the blood flow, followed by subsequent restoration of influx of oxygen/nutrients to the tissue;

conditions of cerebral tissue hypoxia, such as for example, carbon monoxide poisoning or drowning, wherein following normal medical intervention, it is possible to restore normal oxygenation levels;

other tissue damage caused by hypoxia, ischemia or trauma, capable of causing death by apoptosis or autophagy, to the point of generating significant anatomical and functional lesions chronic traumatic encephalopathy (CTE).

A further object of the invention is a cellular culture medium comprising at least one 3-azabicyclo[3.2.1]octan derivative of general formula (I).

A further object of the invention is a storage medium for the preservation of transplanted organs intended for transplantation, said medium comprising at least one 3-azabicyclo[3.2.1]octan derivative of general formula (I).

Object of the invention is also a 3-azabicyclo[3.2.1]octan derivative of general formula (I) labelled with a suitable reagent (contrast agents, radioisotopes, fluorescent agents etc.), for use in any of the procedures useful for the purposes of medical imaging, analysis for imaging of tissues and organs in vitro or in vivo, for the assessment and relevance of the ischemic reperfusion injury and, in particular, to monitor the use and efficacy of the medicinal products.

In the present invention, the expression "amino acid side chain" means the groupings of L or D amino acid side chains present in nature or of the amino acids that are rare or not present in nature.

Unless otherwise specified, the terms alkyl, alkenyl, alkynyl, aryl, arylalkyl, cycloalkyl, and heterocycle, as used in the present invention, should be understood as follows:

- alkyl $C_{1-8}$, alkenyl $C_{1-8}$ and alkynyl $C_{2-8}$ relate to linear branched alkyl radicals, respectively having only single bonds, at least one double bond, at least one triple bond. Examples of alkyl groups according to the present invention include, but are not limited to, methyl, ethyl, propyl, isopropyl, butyl, pentyl, hexyl, heptyl, octyl. Examples of alkenyl groups according to the present invention include, but are not limited to $=CH_2$, ethenyl, propenyl, 1-butenyl, cis-2-butenyl, trans-2-butenyl, 2-methyl-1-propenyl, 1-pentenilel, cis-2-pentenyl, trans-2-pentenyl, 2-methyl-2-butenyl. Examples of alkynyl groups according to the present invention include, but are not limited to, ethynyl, propynyl, 1-butenyl, 2-butynyl, 1-pentenyl, 3-methyl-1-butynyl;
- the term "cycloalkyl" refers to a ring containing carbon atoms, generally having between 3 and 8 members, and preferably between 5 and 6 members. Examples of cycloalkyl groups include, but are not limited to, cyclopropyl, cyclobutyl, cyclopentyl, cyclohexyl, cycloheptyl, cyclooctyl, norbornanyl, camphanyl, adamantanyl;
- the term "aryl" indicates a group containing one or more unsaturated rings, each ring having between 5 and 8 members, preferably 5 or 6 members. Examples of aryl groups include, but are not limited to, phenyl, biphenyl and naphthyl;
- the term "heterocycle" refers to saturated or aromatic heterocycles containing one or more heteroatoms, and preferably one or more N atoms. Examples of heterocycles include, but are not limited to, pyridine, imidazole, pyrrole, indole, triazoles, pyrrolidine, piperidine;

In the present invention, the fluorenylmethoxycarbonyl groups, t-butyloxycarbonyl, carboxybenzyl, benzyl, phenyl and acetyl are respectively indicated using the common terms Fmoc, Boc, Cbz, Bn, Ph and Ac.

According to the present invention, the alkyl, alkenyl, alkynyl, cycloalkyl, aryl and heterocycle groups can be substituted with one or more groupings, and preferably one or two moieties selected from the group consisting of halogen, cyano, nitro, amino, hydroxy, carboxylic acid, carbonyl and $C_{1-6}$ alkyl. The term "halogen" refers to fluorine, chlorine, bromine and iodine.

Of the compounds of formula (I) with R3=COOH there is a preference for those in which:
R1 is selected from the group consisting of H, $C_{1-8}$alkenyl, —$C_{1-8}$alkyl-phenyl, —$C_{1-8}$alkyl-OH and —$C_{1-8}$alkyl-OR;
R2 is selected from the group consisting of aryl, —$C_{1-8}$alkyl-aryl.

Particularly preferred are those in which R1 is selected from the group consisting of H, $C_{1-8}$alkyl, $C_{2-8}$alkenyl, —$C_{1-8}$alkyl-phenyl, —$C_{1-8}$alkyl-OH and —$C_{1-8}$alkyl-OR;
R2 is selected from the group consisting of aryl, —$C_{1-8}$alkyl-aryl;
Of the compounds of formula (I) for use in medical conditions resulting from ischemia-reperfusion, those compounds wherein R1 is selected from the group consisting of H, $C_{1-8}$alkyl, $C_{2-8}$alkenyl, —$C_{1-8}$alkyl-phenyl, —$C_{1-8}$alkyl-OH and —$C_{1-8}$alkyl-OR are preferred;

R2 is selected from the group consisting of aryl and —$C_{1-8}$alkyl-aryl;
R3 is selected from the group consisting of C(O)OR, —C(O)NRR';
R and R', equal to or different from each other, are selected from the group consisting of H, —$C_{1-8}$alkyl, —$C_{1-8}$alkyl-NH2, —$C_{1-8}$alkyl-OH; R and R' combined with each other can form a cycloalkyl.

Particularly preferred are those compounds in which
R1 is H, Me, $=CH2$, CH2Ph, CH2OH, CH2OBn;
R2 is Ph, CH2Ph, CHPh2;
R3 is COOH, COOMe, CONHCH2CH2NH2, CONHCH2CH2OH,

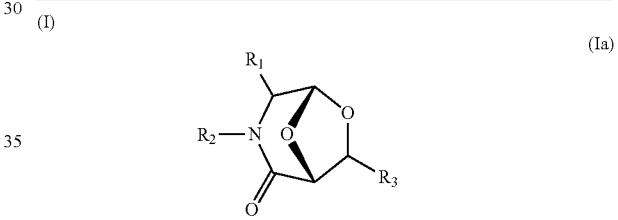

The compounds 1-96 of the general formula (I) according to the invention reported in the following Tables 1-2 are results of particular interest on account of their activities in that they determine a marked increase in the MKP-1 protein; and they are thus the compounds preferably used for the preparation of the pharmaceutical compositions according to the invention.

TABLE (I)

(Ia)

| Compound | $R_1$ | $R_2$ | $R_3$ |
|---|---|---|---|
| 1. | H | PhCH$_2$ | (R)—CO$_2$Me |
| 2. | H | PhCH$_2$ | (S)—CO$_2$Me |
| 3. | H | PhCH$_2$ | 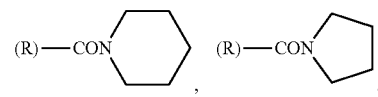 |
| 4. | H | PhCH$_2$ | (R)—CON(pyrrolidinyl) |
| 5. | H | PhCH$_2$ | (R)—CO$_2$H |
| 6. | H | PhCH$_2$ | (S)—CO$_2$H |
| 7. | H | CH(Ph)$_2$ | (R)—CO$_2$H |
| 8. | H | CH(Ph)$_2$ | (S)—CO$_2$H |
| 9. | H | Ph | (R)—CO$_2$H |
| 10. | H | Ph | (S)—CO$_2$H |
| 11. | H | PhCH$_2$ | (R)—CONH(CH$_2$)$_2$NH$_2$ |
| 12. | H | PhCH$_2$ | (R)—CONH(CH$_2$)$_2$OH |
| 13. | (S)—Me | PhCH$_2$ | (R)—CO$_2$Me |
| 14. | (S)—Me | PhCH$_2$ | (S)—CO$_2$Me |
| 15. | (R)—Me | PhCH$_2$ | (R)—CO$_2$Me |
| 16. | (R)—Me | PhCH$_2$ | (S)—CO$_2$Me |
| 17. | (R)—CH$_2$Ph | PhCH$_2$ | (S)—CO$_2$Me |
| 18. | (R)—CH$_2$Ph | PhCH$_2$ | (R)—CO$_2$Me |
| 19. | (S)—CH$_2$Ph | PhCH$_2$ | (S)—CO$_2$Me |
| 20. | (S)—CH$_2$Ph | PhCH$_2$ | (R)—CO$_2$Me |
| 21. | (S)—CH$_2$OBn | PhCH$_2$ | (R)—CO$_2$Me |
| 22. | (S)—CH$_2$OBn | PhCH$_2$ | (S)—CO$_2$Me |
| 23. | (R)—CH$_2$OBn | PhCH$_2$ | (R)—CO$_2$Me |
| 24. | (R)—CH$_2$OBn | PhCH$_2$ | (S)—CO$_2$Me |

TABLE-continued (I)

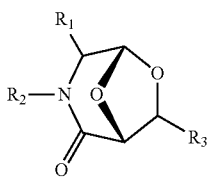

(Ia)

| Compound | R₁ | R₂ | R₃ |
|---|---|---|---|
| 25. | (S)—CH₂OH | PhCH₂ | (R)—CO₂Me |
| 26. | (S)—CH₂OH | PhCH₂ | (S)—CO₂Me |
| 27. | (R)—CH₂OH | PhCH₂ | (R)—CO₂Me |
| 28. | (R)—CH₂OH | PhCH₂ | (S)—CO₂Me |
| 29. | =CH₂ | PhCH₂ | (R)—CO₂Me |
| 30. | =CH₂ | PhCH₂ | (S)—CO₂Me |
| 31. | (S)—Me | PhCH₂ | (R)—CO₂H |
| 32. | (S)—Me | PhCH₂ | (S)—CO₂H |
| 33. | (R)—Me | PhCH₂ | (R)—CO₂H |
| 34. | (R)—Me | PhCH₂ | (S)—CO₂H |
| 35. | (R)—CH₂Ph | PhCH₂ | (S)—CO₂H |
| 36. | (R)—CH₂Ph | PhCH₂ | (R)—CO₂H |
| 37. | (S)—CH₂Ph | PhCH₂ | (S)—CO₂H |
| 38. | (S)—CH₂Ph | PhCH₂ | (R)—CO₂H |
| 39. | (S)—CH₂OBn | PhCH₂ | (R)—CO₂H |
| 40. | (S)—CH₂OBn | PhCH₂ | (S)—CO₂H |
| 41. | (R)—CH₂OBn | PhCH₂ | (R)—CO₂H |
| 42. | (R)—CH₂OBn | PhCH₂ | (S)—CO₂H |
| 43. | (S)—CH₂OH | PhCH₂ | (R)—CO₂H |
| 44. | (S)—CH₂OH | PhCH₂ | (S)—CO₂H |
| 45. | (R)—CH₂OH | PhCH₂ | (R)—CO₂H |
| 46. | (R)—CH₂OH | PhCH₂ | (S)—CO₂H |
| 47. | =CH₂ | PhCH₂ | (R)—CO₂H |
| 48. | =CH₂ | PhCH₂ | (S)—CO₂H |

TABLE 2

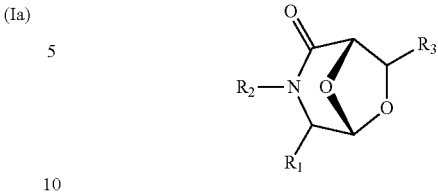

(Ib)

| Compound | R₁ | R₂ | R₃ |
|---|---|---|---|
| 49. | H | PhCH₂ | (R)—CO₂Me |
| 50. | H | PhCH₂ | (S)—CO₂Me |
| 51. | H | PhCH₂ | (R)—CON(piperidinyl) |
| 52. | H | PhCH₂ | (R)—CON(pyrrolidinyl) |
| 53. | H | PhCH₂ | (R)—CO₂H |
| 54. | H | PhCH₂ | (S)—CO₂H |
| 55. | H | CH(Ph)₂ | (R)—CO₂H |
| 56. | H | CH(Ph)₂ | (S)—CO₂H |
| 57. | H | Ph | (R)—CO₂H |
| 58. | H | Ph | (S)—CO₂H |
| 59. | H | PhCH₂ | (R)—CONH(CH₂)₂NH₂ |
| 60. | H | PhCH₂ | (R)—CONH(CH₂)₂OH |
| 61. | (S)—Me | PhCH₂ | (R)—CO₂Me |
| 62. | (S)—Me | PhCH₂ | (S)—CO₂Me |
| 63. | (R)—Me | PhCH₂ | (R)—CO₂Me |
| 64. | (R)—Me | PhCH₂ | (S)—CO₂Me |

TABLE 2-continued (Ib)

| Compound | R₁ | R₂ | R₃ |
|---|---|---|---|
| 65. | (R)—CH₂Ph | PhCH₂ | (S)—CO₂Me |
| 66. | (R)—CH₂Ph | PhCH₂ | (R)—CO₂Me |
| 67. | (S)—CH₂Ph | PhCH₂ | (S)—CO₂Me |
| 68. | (S)—CH₂Ph | PhCH₂ | (R)—CO₂Me |
| 69. | (S)—CH₂OBn | PhCH₂ | (R)—CO₂Me |
| 70. | (S)—CH₂OBn | PhCH₂ | (S)—CO₂Me |
| 71. | (R)—CH₂OBn | PhCH₂ | (R)—CO₂Me |
| 72. | (R)—CH₂OBn | PhCH₂ | (S)—CO₂Me |
| 73. | (S)—CH₂OH | PhCH₂ | (R)—CO₂Me |
| 74. | (S)—CH₂OH | PhCH₂ | (S)—CO₂Me |
| 75. | (R)—CH₂OH | PhCH₂ | (R)—CO₂Me |
| 76. | (R)—CH₂OH | PhCH₂ | (S)—CO₂Me |
| 77. | =CH₂ | PhCH₂ | (R)—CO₂Me |
| 78. | =CH₂ | PhCH₂ | (S)—CO₂Me |
| 79. | (S)—Me | PhCH₂ | (R)—CO₂H |
| 80. | (S)—Me | PhCH₂ | (S)—CO₂H |
| 81. | (R)—Me | PhCH₂ | (R)—CO₂H |
| 82. | (R)—Me | PhCH₂ | (S)—CO₂H |
| 83. | (R)—CH₂Ph | PhCH₂ | (S)—CO₂H |
| 84. | (R)—CH₂Ph | PhCH₂ | (R)—CO₂H |
| 85. | (S)—CH₂Ph | PhCH₂ | (S)—CO₂H |
| 86. | (S)—CH₂Ph | PhCH₂ | (R)—CO₂H |
| 87. | (S)—CH₂OBn | PhCH₂ | (R)—CO₂H |
| 88. | (S)—CH₂OBn | PhCH₂ | (S)—CO₂H |
| 89. | (R)—CH₂OBn | PhCH₂ | (R)—CO₂H |
| 90. | (R)—CH₂OBn | PhCH₂ | (S)—CO₂H |
| 91. | (S)—CH₂OH | PhCH₂ | (R)—CO₂H |
| 92. | (S)—CH₂OH | PhCH₂ | (S)—CO₂H |
| 93. | (R)—CH₂OH | PhCH₂ | (R)—CO₂H |
| 94. | (R)—CH₂OH | PhCH₂ | (S)—CO₂H |
| 95. | =CH₂ | PhCH₂ | (R)—CO₂H |
| 96. | =CH₂ | PhCH₂ | (S)—CO₂H |

The above-cited compounds 1-4, 11-30, 49-52 and 59-78 are described in J. Org. Chem. 1999, 64, 7347, Organic Letters, 2000, 2, 3987-3990, Bioorganic & Med Chem 2001, 9, 1625-1632, Eur. J. Org. Chem. 2002, 873-880, in international patent application no. WO 2001064686; and in international patent application WO2004000324; the methods of preparation of the compounds of formula (I) wherein R3 is different from COOH are also described in these documents.

Compound 5 is cited in J. Org. Chem. 1999, 64, 7347.

The compounds 6-10, 31-48, 53-58, and 79-96 of formula I with R3 equal to COOH are new.

The compounds of formula (I) wherein R3=COOH can be prepared from the compounds of formula (I) wherein R3=COOMe by hydrolysis with NaOH in water and in the presence of linear or cyclic ethers as solvent. The sodium salt is poorly soluble in water and can be isolated by filtration after removal of the organic solvent. By acidification of the compounds of formula (I) wherein R3=COONa, these can be transformed by treatment with aqueous HCl into the corresponding compounds of formula (I) wherein R3=COOH.

The present 3-azabicyco[3.2.1]octan derivatives of general formula (I) in free form or in the form of pharmaceutically acceptable salts can be used for the preparation of pharmaceutical compositions following the usual pharmaceutical preparation methods.

These pharmaceutical compositions can be conventionally formulated, and can include one or more pharmaceutically acceptable excipients and/or diluents. The administration of these formulations can be performed by any conventional route, such as the parenteral route, in the form of solution or suspension, oral, ocular, nasal, topical, etc.

The formulation of the 3-azabicyclo[3.2.1]octan derivatives of formula (I) according to the invention includes tablets, capsules, pills, pellets, solutions, dispersions, suspensions, liposomal formulations, microspheres, nanospheres, creams and ointments, emulsions and aerosols, which can also be prepared in a way that allows a controlled or delayed release of the active compound.

These pharmaceutical compositions can comprise at least one of the present compounds of formula (I), or mixtures thereof, as active ingredient or adjuvant, possibly in combination with another active ingredient or adjuvant, selected according to the pathological conditions.

In addition to use in the previously-indicated pathologies, the 3-azabicyclo[3.2.1]octan derivatives of general formula (I) and mixtures thereof, and thus the compositions that contain them, can be used for the preparation of culture media and storage means useful for the preservation of explanted organs intended for transplantation.

The following examples are reported to provide a non-limiting illustration of the present invention.

Figure 1:
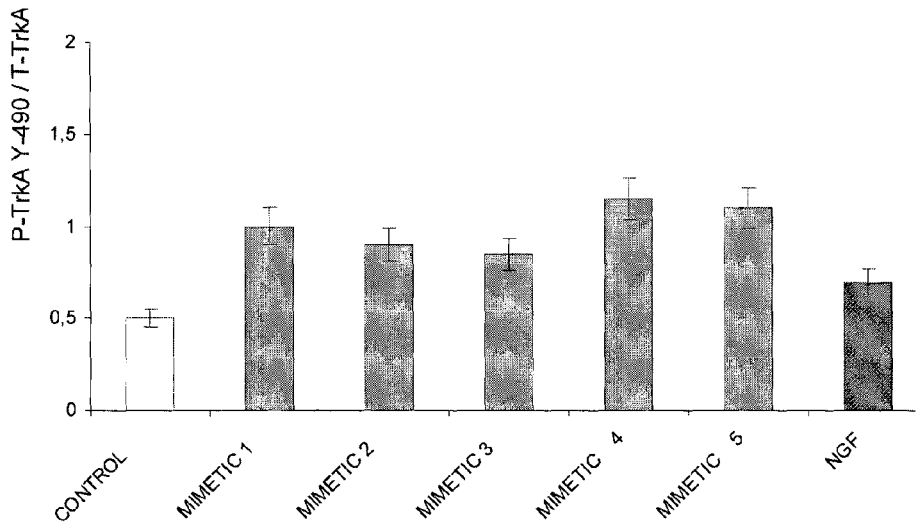
FIG. 1—shows western blotting of Autophosphorylation of the TrkA receptor on PC12 cells when incubated with NGF or with a mimetic (a compound of formula (I)) according to the invention.
Figure 1:
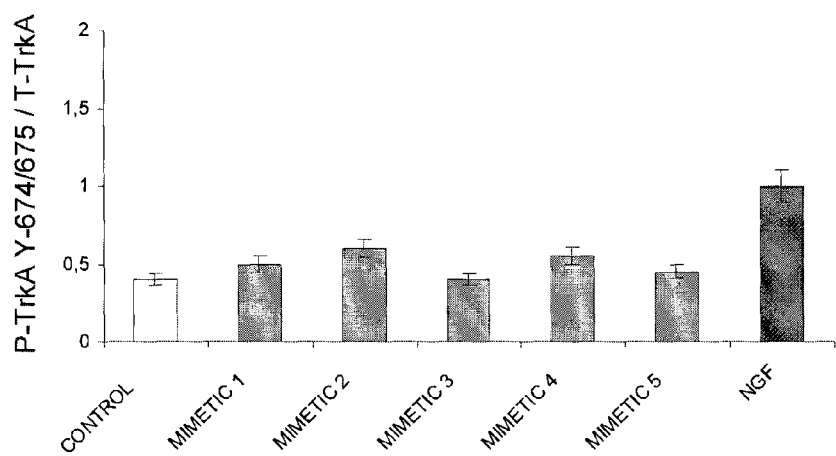
Figure 1:
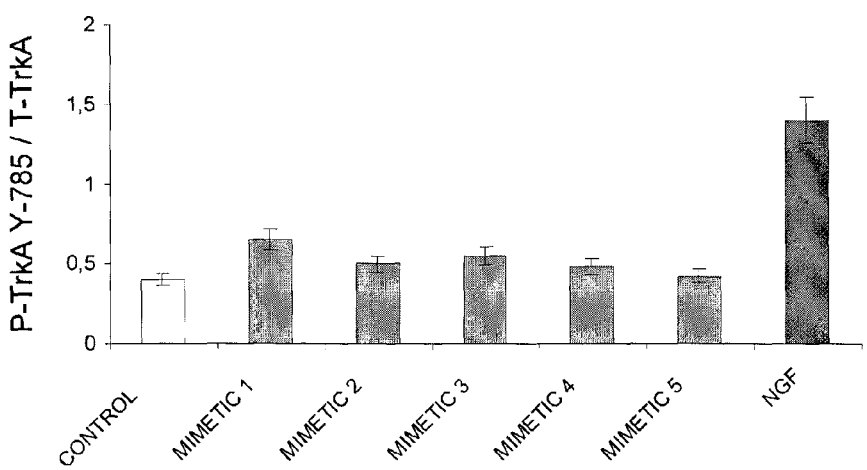

In the above-described drawings, mimetic is a 3-azabicyclo[3.2.1]octan derivative of general formula (I) and in particular Mimetic 1 corresponds to compound 65;

Mimetic 2 corresponds to compound 83;

Mimetic 3 corresponds to compound 19;

Mimetic 4 corresponds to compound 20;

Mimetic 5 corresponds to compound 38.

Example 1

Reference Example

Preparation of (1S,4R,5R,7S)-3,4-dibenzyl-2-oxo-6,8-dioxa-3-azabicyclo[3.2.1]octan-7-sodium carboxylate (compound of formula (I) where $R_1=R_2$ $PhCH_2$ $R_3=(COONa)$)

To a solution of the compound of formula (I), where $R_1=R_2PhCH_2$ $R_3=(COOMe)$ in THF is added dropwise a solution of NaOH in water. After about two hours the reduced pressure solvent completely evaporates and water is added to the residue while leaving under magnetic stirring for 1 h. The resulting solid is filtered and dried to give the compound of formula (I), where $R_1=R_2$ $PhCH_2$ $R_3=$(COONa) m.p. 311.2-313.4° C. (dec.) $[alpha]_D^{21}$+34.3 (c 1.02, DMSO)

Example 2

Preparation of (1S,4R,5R,7S)-3,4-dibenzyl-2-oxo-6,8-dioxa-3-azabicyclo[3.2.1]octan-7-methyl carboxylate (compound of formula (I), where $R_1=R_2$ $PhCH_2$ $R_3=(COOMe)$)

To a suspension of compound I where $R_1=R_2$ $PhCH_2R_3=$COONa in methanol containing a drop of DMF, is added thionyl chloride, without exceeding 40° C. After 30 minutes the solvent is removed under reduced pressure, the residue taken up with toluene and the solvent again removed under reduced pressure. The crude residue is dissolved in toluene and the solution, washed with a saturated aqueous solution of $NaHCO_3$, dried with $MgSO_4$, is evaporated under reduced pressure, thus obtaining compound I with $R_1=R_2$ $PhCH_2$, $R_3=$COOMe in the form of yellow oil.

Example 3

Preparation of (1S,4R,5R,7S-3,4-dibenzyl-2-oxo-6,8-dioxa-3-azabicyclo[3.2.1]octan-7-carboxylic acid (compound of formula (I) where $R_1=R_2$ $PhCH_2R_3$ To a suspension of the compound of formula (I) where $R_1=R_2$ $PhCH_2R_3=$(COONa) in $H_2$, is slowly added HCl 1N until pH 2 is reached. The product is extracted with dichloromethane while maintaining a constant pH, and the organic phase is dried over $Na_2SO_4$. After filtration and evaporation, a compound of formula (I) where $R_1=R_2$ $PhCH_2$ $R_3=$(COOH), is obtained as a white solid.

Example 4

Preparation of (1S,4R,5R,7S)-3,4-dibenzyl-2-oxo-6,8-dioxa-3-azabicyclo[3.2.1]octan-7-lysine carboxylate compound of formula (I) where $R_1=R_2$ $PhCH_2$ $R_3=(COO^-)$ lysine$^+$)

To a solution of compound of formula (I), where $R_1=R_2$ $PhCH_2$ $R_3=$(COOH) in isopropanol, maintained at 65-70° C. and an equivalent solution of L-lysine in water is quickly added. It is cooled in an ice bath and the product is recovered by filtration, after washing with cold isopropanol. The compound product of formula (I), where R1=R2PhCH2 R3= (COO—) lysine+ is obtained. $[alpha]_D^{25}$+29.3 (c 1.0, $H_2O$)

In the following examples, the results of which are also graphically represented in FIGS. 1-5, mimetic means a 3-azabicyclo[3.2.1]octan derivative of general formula (I) and in particular
Mimetic 1 corresponds to compound 65;
Mimetic 2 corresponds to compound 83;
Mimetic 3 corresponds to compound 19;
Mimetic 4 corresponds to compound 20;
Mimetic 5 corresponds to compound 38.

Example 5

Autophosphorylation of the TrkA Receptor and Definition of the Tyrosines Involved in the Process Cells of the continuous PC12 pheochromocytoma rat line were cultured at a concentration of $4 \times 10^5$/ml in RPMI 1640 medium, supplemented with 5% glutamine, antibiotics, and in the absence of serum, in 24-well plates for 6 hours. Subsequently, NGF at a final concentration of 10 ng/ml or alternatively the compounds of formula (I), at the final concentration of 10 μm, were added to these cultures. After 20 minutes, the cells were thus lysed in RIPA buffer (20 mM Tris-HCl, pH 7.5, 150 mM NaCl, 1 mM $Na_2$ EDTA, 1 mM EGTA, 1% NP-40, 1% sodium deoxycholate, 25 mM sodium pyrophosphate, 1 mMβ-glycerophosphate, 1 mM $Na_3VO_4$, 1 μg/ml leupeptin) for biochemical analysis by means of Western blotting (WB) technique, using specific antibodies for the phosphorylated form of the tyrosines 490, 674/675 or 785.

Analysis of the results makes it possible to establish that while NGF invariably induced the phosphorylation of all tyrosines, the compounds of formula I induced the phosphorylation of one of the tyrosines studied but not of others, in different combinations (FIG. 1). The graphs show the phosphorylation values of the indicated tyrosines (Y490, Y674/675, Y785), expressed as the ratio of the intensities of the bands observed in WB, developed with the respective anti-phosphotyrosine antibodies, to the band relating to the total TrkA protein. It is clear that the mimetics very strongly induce the phosphorylation of Y490 and much less that of the other tyrosines. The phosphorylation levels of Y490, but not those of Y674/675 and Y785, induced by the mimetic are significantly higher than the control (p<0.01).

The same experiment, with similar results, was repeated using clones of NIH-3T3 fibroblasts stably transfected with DNA encoding the human TrkA receptor protein.

Example 6

Figure 2:
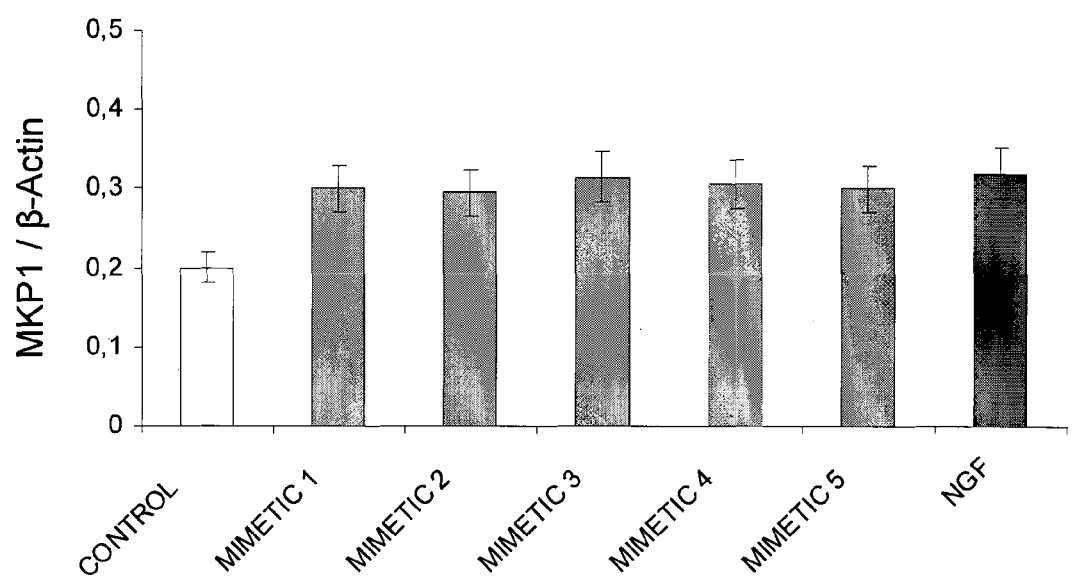
FIG. 2—shows western blotting for the evaluation in PC12 cells to induce an increase in the expression of the MKP-1 protein by mimetics (compounds of formula (I)) according to the invention.

Evaluation of the Ability of the Compounds of Formula (I) to Induce an Increase in MKP-1 Protein Expression PC12 cells were cultured in the absence of serum, exactly as described above in example 5, and then treated for 30 minutes with NGF, at the final concentration of 10 ng/ml, or alternatively with the compounds of formula (I), at the final concentration of 10 μm; subsequently, the cells were lysed, and analysed by WB, using antibodies specific for the MKP-1 protein. The results indicate that the mimetics were capable of inducing an increase in synthesis of MKP-1, to an extent similar to that observed with NGF (FIG. 2). The gel shows the early induction (20 minutes) of the MKP-1 protein in PC12 cells treated with the mimetic compound or with recombinant human NGF. The graph shows the quantitative determination, carried out by means of densitometry, of the gel band is expressed as the ratio of the density of the MKP1 band to that of the β-actin. The MKP-1 protein levels induced by NGF or by the mimetic are significantly higher than the control (p<0.001).

Example 7

Evaluation of the Ability to Induce Dephosphorylation of the p38 MAPK Protein (Activated by Cell Stress)

PC12 cells were cultured in the absence of serum, exactly as described above in example 5, and treated for 30 minutes with NGF, at the final concentration of 10 ng/ml, or alternatively with the compounds of formula I, at the final concentration of 10 μm; the cells were subsequently lysed and analysed by WB, using antibodies specific for the phosphorylated form of the enzyme. The results indicate that the mimetics invariably induced marked dephosphorylation of p38 MAPK, as the native neurotrophin.

Figure 3:
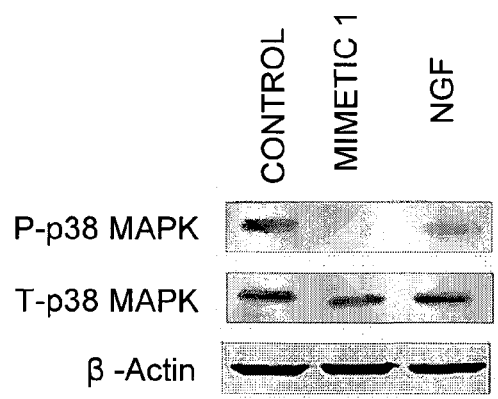
FIG. 3—reports the determination in WB of the phosphorylation levels of the p38 MAPK protein in PC12 cells exposed to serum-deprivation for 6 hours and subsequently to the mimetic (a compound of formula (I)) or to recombinant human NGF for 30 minutes.

FIG. 3 shows the determination in WB of the phosphorylation levels of the p38 MAPK protein in PC12 cells exposed to serum-deprivation for 6 hours and subsequently to the mimetic (a compound of formula (I)) or to recombinant human NGF for 30 minutes. A homogeneity control of protein load on gel, normalisation with β-actin is reported. (FIG. 3).

Example 8

Evaluation of the Activity of an In Vitro Model of Ischemia-Reperfusion on Murine Cardiomyocytes Murine cardiomyocytes, obtained from neonatal mice or from continuous cultures of HL1 cells (murine atrial myxoma), were cultured in triplicate at the concentration of $4 \times 10^5$/ml in RPMI 1640 medium supplemented with 5% glutamine, antibiotics and 10% fetal bovine serum, in 24-well plates, up to the state of confluence. Some plates were then placed at 37° C. for 30 minutes in an incubator containing an artificial atmosphere of air with a partial oxygen pressure equal to 0.5%; another share of cells was cultured under normal conditions as negative control.

Figure 4:
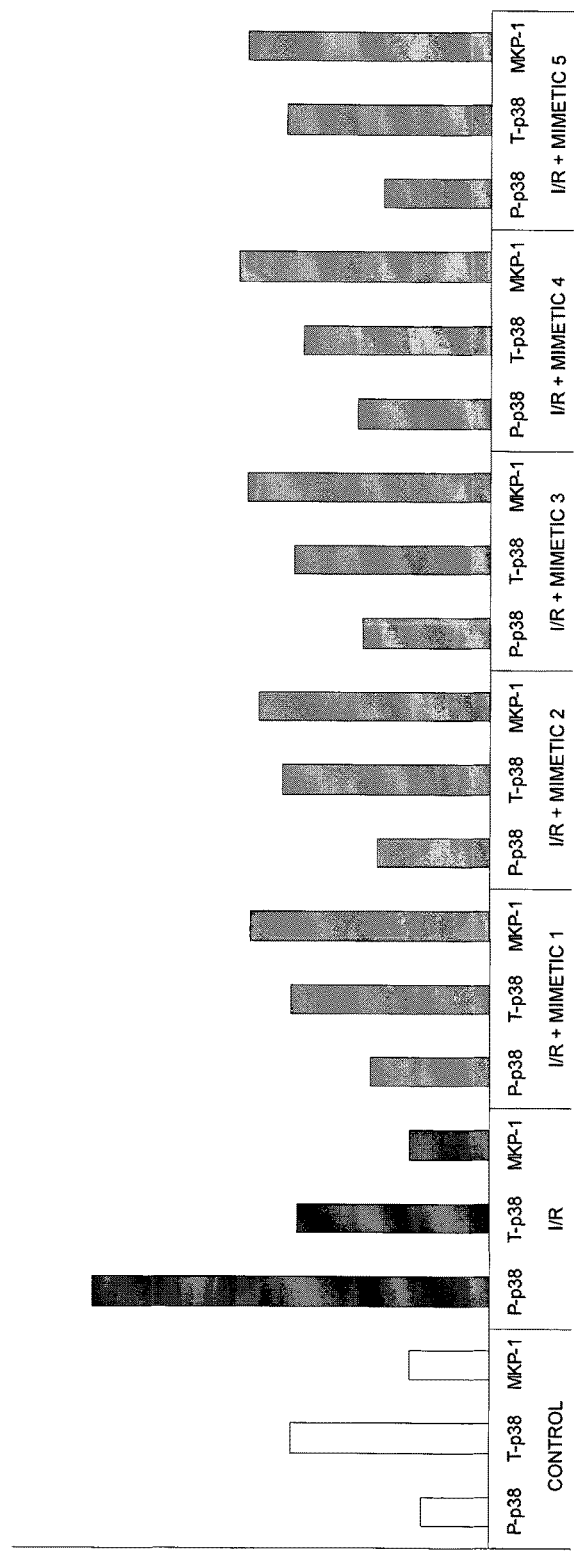
FIG. 4—reports the intensity values of the bands obtained in WB with the indicated antibodies, by analysing samples of cells exposed to ischemia-reperfusion (I/R), in the presence or in the absence of the mimetic compound (a compound of formula (I)), as compared with cells cultured in normal control conditions FIG. 5—shows the histological evaluation at 24 hours of the necrotic damage (upper panels) or apoptotic damage (lower panels) to the right kidney of animals subjected to unilateral ligation of the right renal hilum in the presence or in the absence of the mimetic compound (a compound of formula (I)) (the left kidney served as control) for the times indicated.

The culture period in profound hypoxia having elapsed, some of the cultures were immediately subjected to cell lysis in RIPA buffer to obtain the necessary material for biochemical analysis, while others were cultured in the presence or in the absence of one of the mimetics at a concentration of 5 μm, for a further 3 hours in a normal atmosphere, to evaluate the effect of the reoxygenation/reperfusion, and were then lysed as above; lysates were obtained in parallel from the control cells cultured in normal atmosphere. The three sets of lysates (hypoxia, hypoxia/reperfusion, control) were then processed in WB, obtaining membranes that were exposed to specific antibodies for the p38 MAPK proteins, in phosphorylated or non-phosphorylated form, MKP-1, Bcl-2, Bcl-xL and, as a standardisation control, actin. After further processing for the acquisition of images, the quantitative evaluation of the experimental results was carried out. (FIG. 4).

The graph shows the intensity values of the bands obtained in WB with the indicated antibodies, by analysing samples of cells exposed to ischemia-reperfusion (I/R), in the presence or in the absence of the mimetic compound, as compared with cells cultured in normal control conditions. In the samples treated with the mimetics, there is evident induction of the MKP-1 protein synthesis and the consequent attenuation of the phosphorylation of the p38 MAPK protein. Under the same conditions, NGF induces similar results.

It is evident that there was an evident phosphorylation process of the p38 MAPK protein in the ischemia phase, compared to the controls cultured in normal atmosphere; this activation was further increased after the successive three hours of exposure to normal atmosphere, a procedure that simulates the reperfusion condition. The phenomenon of the increase in the p38 MAPK phosphorylation rate was largely controlled by exposure to the mimetic. Moreover, the marked increase of the MKP-1 protein, a specific phosphatase for the p38 MAPK enzyme, to be thus deemed responsible for the inactivation of the kinase itself, is evident in the same cultures treated.

Example 9

Evaluation of the Efficacy of the Compounds of Formula (I) in Controlling the Apoptotic Phenomenon Induced by the High Presence of Oxygen Reactive Species (ROS)

On another aliquot of cells cultured in hypoxia, with or without treatment, treated as described in example 9, experiments were conducted to assess the efficacy of mimetics in controlling the apoptotic phenomenon induced by the high presence of Reactive Oxygen Species (ROS), which is in turn caused by ischemia and exacerbated by reperfusion. At the end of the reperfusion period, the cells were stained with Annexin-V labelled with fluorescein for 10 minutes, washed, resuspended in an special buffer and analysed by flow cytometry to highlight the cells positive to the dye and thus in active phase of development of the apoptotic process. Analogously to the above-reported results, the cultures treated with NGF or with the mimetic compounds of formula I, capable of inducing increased synthesis of MKP-1, showed a much lower percentage of apoptotic cells than the controls. This data confirms the ability of some mimetics of control the programmed cell death induced by ischemia-reperfusion or by metabolic stress in the broad sense of the word.

Example 10

Figure 5:
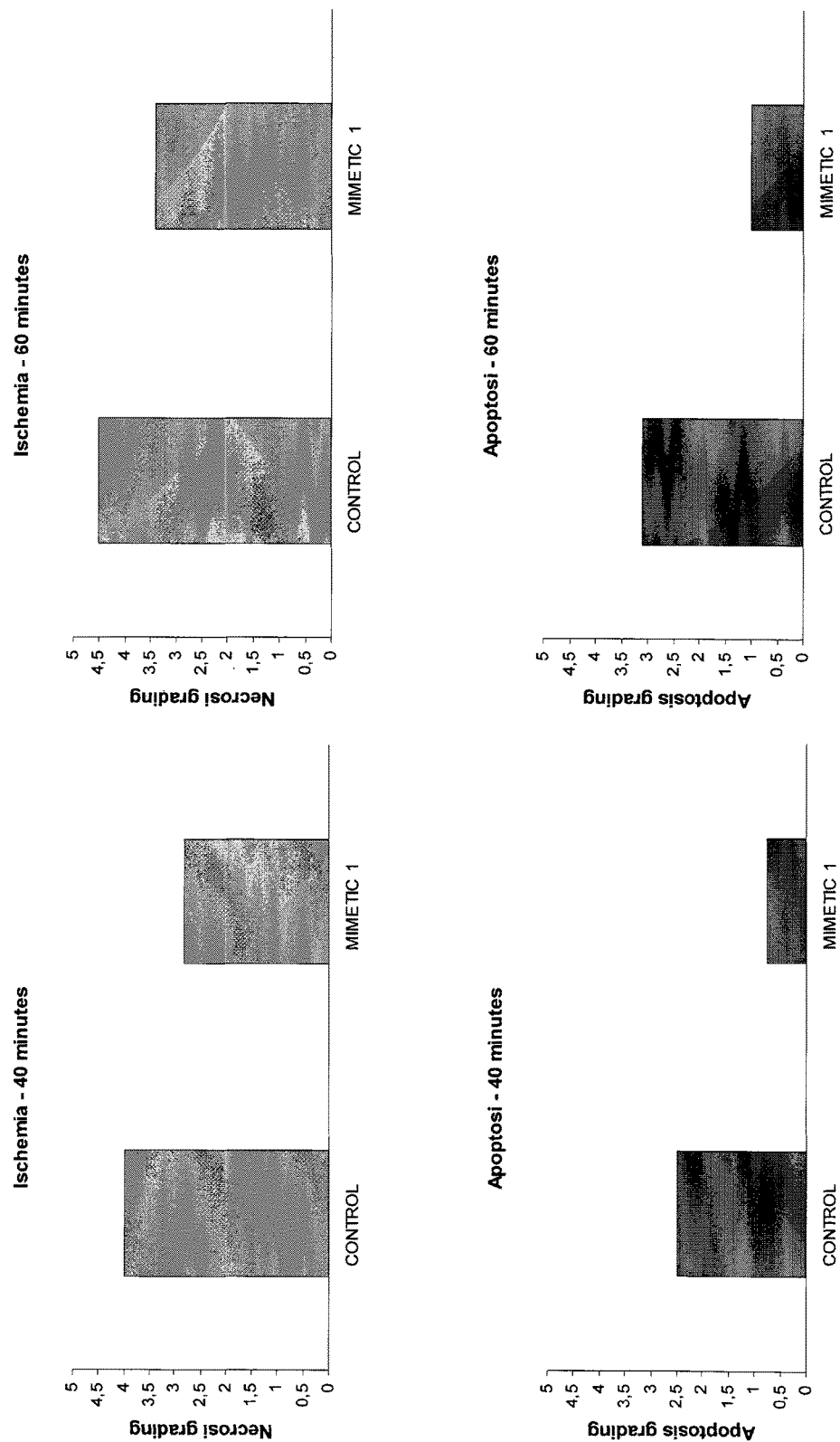

Evaluation of the Effect of the Compounds I in an In Vivo Model of Organ Ischemia-Reperfusion For the purposes of demonstrating the efficacy of the mimetics of formula (I) in controlling the apoptotic phenomenon induced by ischemia-reperfusion in an organ, the warm kidney murine ischemisation model was used. In short, 6 C57Bl6 eight-week old male mice were subjected to unilateral closure, by clamping, of the renal hilum, while keeping the organ in situ ("warm" ischemia); this condition was maintained for 40 minutes, at the end of which the blood flow was restored. Three of the animals were injected with one of the mimetics of formula (I) capable of inducing in vivo increase in MKP-1 protein synthesis, at a dose of 1 mg/kg of body weight, while the remaining animals were injected with a similar volume of the buffer used to solubilise the compound, as control. The animals were then kept under observation for 24 hours and, then euthanised. Both the ischemised organ and the contralateral organ, as control, were then prepared for histological examination, with a view to determining the intensity of the necrotic and apoptotic damage induced by the ischemic-reperfusion, both evaluated by means of the use of the scale typically employed for carrying out the grading of the histological damage. The extensive analysis of the histological preparations highlighted a marked level of cellular damage, both necrotic and apoptotic, to the glomerular structures and to the tubular structures, in the control organs. In the organs obtained from the animals treated with the mimetic, on the other hand, there was an evident marked reduction of the intensity of the apoptotic damage, while the levels of necrotic damage were comparable to those of the control organs (FIG. 5). It is evident that the necrotic damage is substantially unchanged by treatment with the mimetic, while the apoptotic damage is strongly modulated by the pharmacological activity of the compound, at statistically significant levels ($p<0.001$). These observations confirm, even in an in vivo ischemia-reperfusion model, the effectiveness of certain mimetics of formula 1 in the modulation of the apoptotic damage and thus induce to extend the use thereof for the treatment of organs intended for transplantation, for the purposes of obtaining an improved state of preservation thereof.

The invention claimed is:

1. A compound designated as (1S,4R,5R,7S)-3,4-dibenzyl-2-oxo-6,8-dioxa-3-azabicyclo[3.2.1]octan-7 carboxylic acid or a pharmaceutically acceptable salt thereof.

2. A compound designated as (1S,4R,5R,7S)-3,4-dibenzyl-2-oxo-6,8-dioxa-3-azabicyclo[3.2.1]octan-7-lysine carboxylate.

3. A pharmaceutical composition comprising a compound of formula (I)

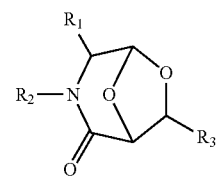

I wherein $R_1$ is selected from the group consisting of H, Me, $=CH_2$, $CH_2Ph$, $CH_2OH$ and $CH_2OBn$;

$R_2$ is selected from the group consisting of Ph, $CH_2Ph$ and $CHPh_2$;

$R_3$ is COOH;

wherein said phenyl can be substituted by one or more group selected from the group consisting of halogen, CN, $NO_2$, $NH_2$, OH, COOH, CO and $C_{1-6}$alkyl;

or a pharmaceutically acceptable salt thereof;

and at least one pharmaceutically acceptable excipient.

4. The pharmaceutical composition according to claim 3, wherein the compound of formula (I) is characterized by formula (Ia)

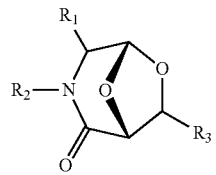

Ia wherein

| R₁ | R₂ | R₃ |
|---|---|---|
| H | PhCH₂ | (R) —CO₂H |
| H | PhCH₂ | (S) —CO₂H |
| H | CH(Ph)₂ | (R) —CO₂H |
| H | CH(Ph)₂ | (S) —CO₂H |
| H | Ph | (R) —CO₂H |
| H | Ph | (S) —CO₂H |
| (S) —Me | PhCH₂ | (R) —CO₂H |
| (S) —Me | PhCH₂ | (S) —CO₂H |
| (R) —Me | PhCH₂ | (R) —CO₂H |
| (R) —Me | PhCH₂ | (S) —CO₂H |
| (R) —CH₂Ph | PhCH₂ | (S) —CO₂H |
| (R) —CH₂Ph | PhCH₂ | (R) —CO₂H |
| (S) —CH₂Ph | PhCH₂ | (S) —CO₂H |
| (S) —CH₂Ph | PhCH₂ | (R) —CO₂H |
| (S)—CH₂OBn | PhCH₂ | (R) —CO₂H |
| (S)—CH₂OBn | PhCH₂ | (S) —CO₂H |
| (R)—CH₂OBn | PhCH₂ | (R) —CO₂H |
| (R)—CH₂OBn | PhCH₂ | (S) —CO₂H |
| (S)—CH₂OH | PhCH₂ | (R) —CO₂H |
| (S)—CH₂OH | PhCH₂ | (S) —CO₂H |
| (R)—CH₂OH | PhCH₂ | (R) —CO₂H |
| (R)—CH₂OH | PhCH₂ | (S) —CO₂H |
| =CH₂ | PhCH₂ | (R) —CO₂H |
| =CH₂ | PhCH₂ | (S) —CO₂H. |

5. The pharmaceutical composition according to claim 3, wherein the compound of formula (I) is characterized by formula (Ib)

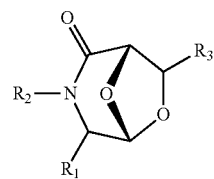

wherein

| R1 | R2 | R3 |
|---|---|---|
| H | PhCH₂ | (R)—CO₂H |
| H | PhCH₂ | (S)—CO₂H |
| H | CH(Ph)₂ | (R)—CO₂H |
| H | CH(Ph)₂ | (S)—CO₂H |
| H | Ph | (R)—CO₂H |
| H | Ph | (S)—CO₂H |
| (S)—Me | PhCH₂ | (R)—CO₂H |
| (S)—Me | PhCH₂ | (S)—CO₂H |
| (R)—Me | PhCH₂ | (R)—CO₂H |
| (R)—Me | PhCH₂ | (S)—CO₂H |
| (R)—CH₂Ph | PhCH₂ | (S)—CO₂H |
| (R)—CH₂Ph | PhCH₂ | (R)—CO₂H |
| (S)—CH₂Ph | PhCH₂ | (S)—CO₂H |
| (S)—CH₂Ph | PhCH₂ | (R)—CO₂H |
| (S)—CH₂Obn | PhCH₂ | (R)—CO₂H |
| (S)—CH₂Obn | PhCH₂ | (S)—CO₂H |
| (R)—CH₂Obn | PhCH₂ | (R)—CO₂H |
| (R)—CH₂Obn | PhCH₂ | (S)—CO₂H |
| (S)—CH₂OH | PhCH₂ | (R)—CO₂H |
| (S)—CH₂OH | PhCH₂ | (S)—CO₂H |
| (R)—CH₂OH | PhCH₂ | (R)—CO₂H |
| (R)—CH₂OH | PhCH₂ | (S)—CO₂H |
| =CH₂ | PhCH₂ | (R)—CO₂H |
| =CH₂ | PhCH₂ | (S)—CO₂H. |

6. A composition comprising the compound of claim 1, and a pharmaceutically acceptable excipient.

7. A composition comprising the compound of claim 2, and a pharmaceutically acceptable excipient.

8. A method for treating an ischemia-reperfusion-related pathology or a surgical procedure involving ischemia-reperfusion injury, said method comprising administering to a patient in need thereof an effective amount of a compound of formula (I)

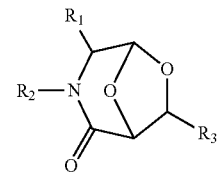

wherein
R₁ is selected from the group consisting of H, Me, =CH₂, CH₂Ph, CH₂OH and CH₂OBn;
R₂ is selected from the group consisting of Ph, CH₂Ph and CHPh₂;
R₃ is COOH;
wherein said phenyl can be substituted by one or more group selected from the group consisting of halogen, CN, NO₂, NH₂, OH, COOH, CO and C₁₋₆alkyl;
or a pharmaceutically acceptable salt thereof;
excluding the compound (1 R5S,7R)-3-Benzyl-2-oxo-6, 8-dioxa-3-azabicyclo[3.2.1]octan-7-carboxylic acid.

9. The method according to claim 8, wherein the compound of formula I is characterized by formula (Ia)

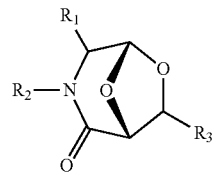

| Compound | R1 | R2 | R3 |
|---|---|---|---|
| 5 | H | PhCH₂ | (R)—CO₂H |
| 6 | H | PhCH₂ | (S)—CO₂H |
| 7 | H | CH(Ph)₂ | (R)—CO₂H |
| 8 | H | CH(Ph)₂ | (S)—CO₂H |
| 9 | H | Ph | (R)—CO₂H |
| 10 | H | Ph | (S)—CO₂H |
| 31 | (S)—Me | PhCH₂ | (R)—CO₂H |
| 32 | (S)—Me | PhCH₂ | (S)—CO₂H |
| 33 | (R)—Me | PhCH₂ | (R)—CO₂H |
| 34 | (R)—Me | PhCH₂ | (S)—CO₂H |
| 35 | (R)—CH₂Ph | PhCH₂ | (S)—CO₂H |
| 36 | (R)—CH₂Ph | PhCH₂ | (R)—CO₂H |
| 37 | (S)—CH₂Ph | PhCH₂ | (S)—CO₂H |
| 38 | (S)—CH₂Ph | PhCH₂ | (R)—CO₂H |
| 39 | (S)—CH₂Obn | PhCH₂ | (R)—CO₂H |
| 40 | (S)—CH₂Obn | PhCH₂ | (S)—CO₂H |
| 41 | (R)—CH₂Obn | PhCH₂ | (R)—CO₂H |
| 42 | (R)—CH₂Obn | PhCH₂ | (S)—CO₂H |
| 43 | (S)—CH₂OH | PhCH₂ | (R)—CO₂H |
| 44 | (S)—CH₂OH | PhCH₂ | (S)—CO₂H |
| 45 | (R)—CH₂OH | PhCH₂ | (R)—CO₂H |
| 46 | (R)—CH₂OH | PhCH₂ | (S)—CO₂H |
| 47 | =CH₂ | PhCH₂ | (R)—CO₂H |
| 48 | =CH₂ | PhCH₂ | (S)—CO₂H. |

10. The method according to claim 8, wherein the compound of formula I is characterized by formula (Ib)

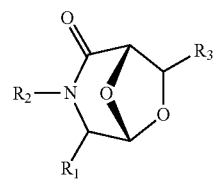

Ib wherein

| Compound | R1 | R2 | R3 |
|---|---|---|---|
| 53 | H | PhCH₂ | (R)—CO₂H |
| 54 | H | PhCH₂ | (S)—CO₂H |
| 55 | H | CH(Ph)₂ | (R)—CO₂H |
| 56 | H | CH(Ph)₂ | (S)—CO₂H |
| 57 | H | Ph | (R)—CO₂H |
| 58 | H | Ph | (S)—CO₂H |
| 79 | (S)—Me | PhCH₂ | (R)—CO₂H |
| 80 | (S)—Me | PhCH₂ | (S)—CO₂H |
| 81 | (R)—Me | PhCH₂ | (R)—CO₂H |
| 82 | (R)—Me | PhCH₂ | (S)—CO₂H |
| 83 | (R)—CH₂Ph | PhCH₂ | (S)—CO₂H |
| 84 | (R)—CH₂Ph | PhCH₂ | (R)—CO₂H |
| 85 | (S)—CH₂Ph | PhCH₂ | (S)—CO₂H |
| 86 | (S)—CH₂Ph | PhCH₂ | (R)—CO₂H |
| 87 | (S)—CH₂Obn | PhCH₂ | (R)—CO₂H |
| 88 | (S)—CH₂Obn | PhCH₂ | (S)—CO₂H |
| 89 | (R)—CH₂Obn | PhCH₂ | (R)—CO₂H |
| 90 | (R)—CH₂Obn | PhCH₂ | (S)—CO₂H |
| 91 | (S)—CH₂OH | PhCH₂ | (R)—CO₂H |
| 92 | (S)—CH₂OH | PhCH₂ | (S)—CO₂H |
| 93 | (R)—CH₂OH | PhCH₂ | (R)—CO₂H |
| 94 | (R)—CH₂OH | PhCH₂ | (S)—CO₂H |
| 95 | =CH₂ | PhCH₂ | (R)—CO₂H |
| 96 | =CH₂ | PhCH₂ | (S)—CO₂H. |

11. The method according to claim 8, wherein said pathology or surgical procedure is selected from the group consisting of:
acute myocardial ischemia;
acute hypoxic renal injury;
acute hypoxic pulmonary injury;
acute hypoxic intestinal injury;
central nervous system (CNS) ischemia caused by thrombosis or embolism in a cerebral district of a intracranial artery or by cardiac arrest,
a cerebral tissue hypoxia condition;
other tissue damage caused by hypoxia, ischemia or trauma,
organ transplantation,
chronic traumatic encephalopathy (CTE),
multiple organ dysfunction syndrome (MODS), and
compartment syndrome of the extremity (CSE).

12. The method of claim 8, wherein said surgical procedure involving ischemia-reperfusion injury is selected from the group consisting of renal tumor ablation surgery and cardiac surgery.

13. The method of claim 8, wherein said ischemia-reperfusion-related pathology is selected from the group consisting of glaucoma, sickle cell disease (SCD) retinopathy, diabetic retinopathy, a cutaneous pressure ulcer, a vascular lesion of a limb, a disease caused by acute or chronic alteration of blood flow in the splanchnic district and Diffuse Intravascular Coagulation (DIC) followed by subsequent restoration of influx.

14. A storage medium for the preservation of an explanted organ, supplemented with at least one compound of formula (I)

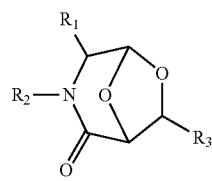

I wherein
$R_1$ is selected from the group consisting of H, Me, =CH₂, CH₂Ph, CH₂OH and CH₂OBn;
$R_2$ is selected from the group consisting of Ph, CH₂Ph and CHPh₂;
$R_3$ is COOH;
wherein said phenyl can be substituted by one or more group selected from the group consisting of halogen, CN, NO₂, NH₂, OH, COOH, CO and $C_{1-6}$alkyl;
or a pharmaceutically acceptable salt thereof;
excluding the compound (1 R5S,7R)-3-Benzyl-2-oxo-6, 8-dioxa-3-azabicyclo[3.2.1]octan-7-carboxylic acid.

15. A cell culture medium supplemented with at least one compound of formula (I)

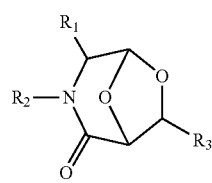

I wherein
$R_1$ is selected from the group consisting of H, Me, =CH₂, CH₂Ph, CH₂OH and CH₂OBn;
$R_2$ is selected from the group consisting of Ph, CH₂Ph and CHPh₂;
$R_3$ is COOH;
wherein said phenyl can be substituted by one or more group selected from the group consisting of halogen, CN, NO₂, NH₂, OH, COOH, CO and $C_{1-6}$alkyl;
or a pharmaceutically acceptable salt thereof;
excluding the compound (1 R5S,7R)-3-Benzyl-2-oxo-6, 8-dioxa-3-azabicyclo[3.2.1]octan-7-carboxylic acid.

* * * * *